United States Patent
Del Bono et al.

(10) Patent No.: US 11,045,513 B2
(45) Date of Patent: Jun. 29, 2021

(54) ASSOCIATION OF DRY EXTRACTS OF VICIA FABA, UNCARIA RHYNCOPHYLLA AND LIQUORICE ROOT TOGETHER WITH COENZYME Q10 FOR USE AS COADJUVANT, FOR IMPROVING THE QUALITY OF LIFE IN SUBJECTS SUFFERING FROM MOVEMENT DISORDERS

(71) Applicant: CRISTALFARMA S.R.L., Milan (IT)

(72) Inventors: Maria Cristina Del Bono, Milan (IT); Francesco Bonomo, Milan (IT)

(73) Assignee: CRISTALFARMA S.R.L., Milan (IT)

(*) Notice: Subject to any disclaimer, the term of this patent is extended or adjusted under 35 U.S.C. 154(b) by 0 days.

(21) Appl. No.: 16/970,669

(22) PCT Filed: Feb. 20, 2019

(86) PCT No.: PCT/IB2019/051381
§ 371 (c)(1),
(2) Date: Aug. 18, 2020

(87) PCT Pub. No.: WO2019/162852
PCT Pub. Date: Aug. 29, 2019

(65) Prior Publication Data
US 2020/0376062 A1    Dec. 3, 2020

(30) Foreign Application Priority Data

Feb. 22, 2018 (IT) .......................... 102018000002947

(51) Int. Cl.
| | |
|---|---|
| A61K 36/48 | (2006.01) |
| A23L 33/105 | (2016.01) |
| A23L 33/15 | (2016.01) |
| A61P 25/16 | (2006.01) |
| A61K 9/00 | (2006.01) |
| A61K 31/122 | (2006.01) |
| A61K 31/19 | (2006.01) |
| A61K 31/355 | (2006.01) |
| A61K 31/375 | (2006.01) |
| A61K 36/484 | (2006.01) |
| A61K 36/74 | (2006.01) |

(52) U.S. Cl.
CPC ............ *A61K 36/48* (2013.01); *A23L 33/105* (2016.08); *A23L 33/15* (2016.08); *A61K 9/009* (2013.01); *A61K 31/122* (2013.01); *A61K 31/19* (2013.01); *A61K 31/355* (2013.01); *A61K 31/375* (2013.01); *A61K 36/484* (2013.01); *A61K 36/74* (2013.01); *A61P 25/16* (2018.01); *A23V 2002/00* (2013.01)

(58) Field of Classification Search
CPC .......... A23V 2200/30; A23V 2250/252; A61P 25/16; A61P 25/00
USPC .................. 424/725, 752; 514/456
See application file for complete search history.

(56) References Cited

U.S. PATENT DOCUMENTS

| | | | |
|---|---|---|---|
| 2003/0017998 A1* | 1/2003 | Snow | ................... A61K 31/353 514/27 |
| 2007/0116779 A1 | 5/2007 | Mazzio | |
| 2008/0118583 A1 | 5/2008 | Rangel | |

FOREIGN PATENT DOCUMENTS

| | | |
|---|---|---|
| CN | 101549082 A | 10/2009 |
| CN | 104173419 A | 12/2014 |
| CN | 104738747 A | 7/2015 |
| EP | 3225245 A1 | 10/2017 |

OTHER PUBLICATIONS

Michael J. Aminoff, "Treatment of Parkinson's Disease." Neurology Therapy: 161;303-308; 1994. (Year: 1994).*
Kempster P.A. et al., "Motor effects of broad beans (Vicia faba) in Parkinson's disease: single dose studies", Asia Pacific Journal of Clinical Nutri, Smith-Gordon Journal, London, GB, vol. 2, No. 2, Jun. 1, 1993, pp. 85-89.
Search Report and Written Opinion of PCT/IB2019/051381 dated Nov. 21, 2019.
Shim J.S. et al., "Effects of the hook of Uncaria rhynchophylla on neurotoxicity in the 6-hydroxydopamine model of Parkinson's disease", Journal of Ethnopharmacology, Elsevier Ireland, Ltd, IE. vol. 126, No. 2, Nov. 12, 2009, pp. 361-365.

* cited by examiner

*Primary Examiner* — Walter E Webb
(74) *Attorney, Agent, or Firm* — Silvia Salvadori, P.C.; Silvia Salvadori

(57) ABSTRACT

Association comprising: —dry extract of: a) *Vicia faba*, b) *Uncaria rhyncophylla* and c) liquorice root, —coenzyme Q10, and preferably at least one vitamin chosen from vitamin C and E for use as coadjuvant for improving the quality of life (QOL) in subjects with movement disorders and in particular in subjects suffering from Parkinson's disease. This association is preferably in an oral formulation, more preferably in the form of a food supplement.

7 Claims, 2 Drawing Sheets

ASSOCIATION OF DRY EXTRACTS OF VICIA FABA, UNCARIA RHYNCOPHYLLA AND LIQUORICE ROOT TOGETHER WITH COENZYME Q10 FOR USE AS COADJUVANT, FOR IMPROVING THE QUALITY OF LIFE IN SUBJECTS SUFFERING FROM MOVEMENT DISORDERS

This application is a U.S. national stage of PCT/IB2019/051381 filed 20 Feb. 2019, which claims priority to and the benefit of Italian Application No. 102018000002947 filed on 22 Feb. 2018, the contents of which are incorporated herein by reference in their entireties.

DESCRIPTION

The present invention relates to an oral formulation and in particular a food supplement for use as coadjuvant for improving the quality of life (QOL) in subjects with movement disorders and in particular in subjects suffering from Parkinson's disease.

STATE OF THE ART

The term movement disorders groups together a vast number of diseases characterized by reduced motor skills and/or by the presence of involuntary movements, namely movements that are hardly controllable with willpower. Among the most well-known forms, parkinsonian syndromes constitute a vast chapter of modern neurological nosology[1]. There are distinguished primary forms (Parkinson's disease, multi systemic atrophy, progressive supranuclear palsy, cortico-basal degeneration, dementia with lewy bodies), secondary forms (so-called vascular, infectious, post-infectious, post-traumatic parkinsonisms, parkinsonisms due to non-conventional agents, parkinsonisms due to environmental, iatrogenic, metabolic toxic factors) and forms of parkinsonism associated with hereditary diseases of the central nervous system (Wilson's disease, Westphal variant of Huntington's, Hallervorden Spatz disease). The best known of these diseases is Parkinson's disease[1]. Parkinson's disease is defined as a degenerative disease of the nervous system with a slow and progressive evolution. A particular structure of the brain, the black substance, undergoes a progressive loss of the nerve cells that compose it. These cells produce a substance, dopamine, a fundamental neurotransmitter so that motor activity can develop rapidly and harmoniously. Therefore, its deficiency leads to a reduction in automatic motor activity, muscle stiffness, slowness in the execution of voluntary movements and tremors[1]. From a biochemical point of view, a reduction in the quantity of dopamine, a loss of the characteristic pigmentation (lower neuromelanin concentration), a reduction in the activity of the complex I of the mitochondrial respiratory chain and a lower activity of α-ketoglutarate dehydrogenase[2] have been ascertained at the level of the SNpc (Substantia Nigra pars compacta) of parkinsonian subjects. Mitochondria are a remarkable source of ROS. These species, besides causing oxidative damage, inhibit mitochondrial function by inducing the release of excitatory amino acids such as glutamate and aspartate, which, in turn, cause an increase in $Ca^{+2}$ free in the cytosol, leading to a series of events that trigger neuronal degeneration[2]. And it is precisely all that is observed in the parkinsonian patient[1,2]. Age-specific prevalence analysis highlights how Parkinson's disease is clearly prevalent in the age groups above 60, while sex-specific rates show a slight prevalence in men. In conclusion, in Italy on the basis of the most accurate epidemiological studies and considering the resident population at the last census, they can be estimated about 170,000 prevalent cases[1].

The older treatment of this type of pathology is definitely the treatment with Levodopa or L-dopa, which is decarboxylated to dopamine within the dopaminergic presynaptic neurons in the striatum responsible for the therapeutic efficacy of the drug in Parkinson's disease. The plasma concentrations of levodopa are between 0.5 and 2 hours and half-life is between 1 and 3 hours. This treatment is generally associated with a peripheral dopa carboxylase inhibitor (carbidopa or benserazide), which decreases the peripheral side effects of L-dopa[8].

Another type of treatment involves the administration of selegiline, a monoamine oxidase inhibitor (MAO inhibitor), in the specific a B-MAO inhibitor. This mechanism of action protects dopamine from intraneuronal degradation, thereby reducing the metabolism of dopamine[8].

Other types of drugs for the treatment of Parkinson's disease are dopamine agonist receptors, such as e.g. bromocriptine and some newer ones, such as ropinirole pramipexole, rotigotine and apomorphine.

Another type of treatment involves the administration of amantadine, which has multiple mechanisms of action such as: increased release of dopamine, inhibition of amine up-take, a direct action on dopamine receptors and finally inhibition of glutamine receptors of the N-methyl-aspartate type[8].

Although these drugs are effective, they have considerable side effects in the long run.

The need is therefore felt to have available oral formulations, such as for example food supplements which, administered daily, allow reducing the daily dosage of the aforementioned drugs, thereby reducing the side effects, thus allowing to improve the QOL in subjects suffering from movement disorders.

It is also known that the broad bean (*Vicia faba*) is a natural source of Levodopa (L-Dopa). It has been shown how the clinical use of the broad bean contributes to raising the plasma levels of L-dopa and to improving the motor functions of parkinsonian subjects[3,4,5]. The average content of L-dopa in broad beans as a food is in the range of 1.43-1.51 mg/dl of aqueous extract, so that it is hypothesized its rational use as a food treatment of Parkinson's disease[6].

The aqueous extract of *Uncaria rhynchophylla* significantly protects dopaminergic neurons when insulted by 6-hydroxydopamine (6-OHDA), a neurotoxin used to construct models of Parkinson's disease[7]. The aqueous extract of *Uncaria rhynchophylla* can therefore exert an important neuroprotective effect for the treatment of clinical parkinsonism. The biological mechanisms employed by *Uncaria rhyncophylla* also concern the rise in plasma levels of dopamine, the normalization of the activity of the mitochondrial-I complex and of the level of glutathione (tripeptide with antioxidant properties)[8]. There is evidence that attribute to *Uncaria rhyncophylla* a potential activity to promote the clearance of alpha-synuclein (a small protein that is normally found in presynaptic nerve endings, where it is thought to play a role in the transmission of nerve impulses. In Parkinson's disease, alpha-synuclein tends to aggregate, forming larger oligomers that create typical deposits in diseased neurons called lewy bodies)[9].

The glycyrrhetinic acid contained in liquorice has shown a strong binding affinity for the dopamine D3 receptor (DRD3). D3 dopaminergic receptors come into play in a series of neurological processes such as: motivation, pleasure, cognitive processes, memory, learning, movement control and regulation of neuroendocrine signalling pathways and are among the main targets of the drugs that treat Parkinson's disease[10]. Moreover, liquorice has a specific anti-inflammatory action on microglial cells (dealing with the first and main immune defense active in the central nervous system) and has a reducing action on glutamate-mediated excitotoxicity associated with neuronal cell death of the hippocampus[11].

Several evidences suggest that mitochondria dysfunctions and oxidative stress play a central role in the dopaminergic neurodegeneration of Parkinson's disease. Among the non-enzymatic antioxidants active in countering the development of free radicals at the mitochondrial level are vitamin C, vitamin E and coenzyme Q10. Vitamin E acts with a radical scavenging mechanism, stabilizing the peroxidic radicals, peroxynitrite and hydroxyl radicals, thus inhibiting the propagation of the radical chain and the establishment of lipid peroxidation on the membranes[12]. A second antioxidant is vitamin C, which works in association with vitamin E to regenerate α-tocopherol from the α-tocopherol radical[12]. As for coenzyme Q10, its antioxidant activity derives from the ability to exchange two electrons in a redox cycle between its oxidized form (ubiquinone) and its reduced form (ubiquinol). Ubiquinol is a powerful antioxidant that reduces the process of lipid peroxidation and inhibits the oxidation of DNA proteins[12]. The integration of these non-enzymatic antioxidants is identified as a valid tool to protect the neurological degeneration underlying Parkinson's disease[12].

US 20087118583 concerns a phytonutraceutical formed by the association of three types of beneficial plants, namely the type E plants, in other words those capable of enhancing energy, those capable of enhancing bio-intelligence (I) and finally those capable of guaranteeing energy organization (O). The exemplified composition which falls under the aforementioned definitions and is exemplified in Table I contains the *Uncaria tormentosa* and the coenzyme Q10.

US 2007/11679 concerns a nutraceutical to mitigate specific factors of the degenerative process that occurs in Parkinson's disease, containing as active ingredients pyruvate, succinate oxaloacetate in association with micronutrients, oligo elements, amino acids, flavonoids and plant concentrates.

EP 3225245 describes an extract obtained from *Vicia faba* and its use in the treatment and/or in the prevention of degenerative diseases, possibly in the presence of vitamin E.

CN104173419 discloses tablets including bean sprout and flower powders as a source of L-dopa, for the treatment of Parkinson's disease, CN101549082 claims a composition for the treatment of Parkinson's disease, comprising veratrum and liquorice.

CN104738747 discloses a broad bean flower drink containing vitamin C, citric acid and finally sucrose, to prevent and control Parkinson's disease and it does not anticipate the invention at all.

Kempster P. et al in "Motor effects of broad beans (*Vicia faba*) in Parkinson's disease: single dose studies. ASIA PACIFIC JOURNAL OF CLINICAL NUTRITION SMITH GORDON-JOURNAL, London, GB, pages 85-89 no. 2, 1 June, XP009191250 ISSN: 0378-8741, DOI10.106/JEP 2009.08.23, retrieved on 2009 Aug. 22) describe a study on the motor effects of patients suffering from Parkinson's disease who had been given 100 to 200 g of broad beans and carbidopa. Shim et al in "Effects of the hook of *Uncaria rhynchophylla*" report that the extract of this plant considerably reduces cell death and ROS generation; increases GSH levels, inhibiting the activity of caspase-3 induced by 6-OHDA (6-hydroxydopamine), significantly reduces induced apomorphine rotation and lowers neuronal dopaminergic loss in the Substantia Nigra pars compacta. This demonstrates that this extract exerts a neuroprotective activity against 6-OHDA-induced neurotoxicity through antioxidative and antiapoptosis mechanisms in Parkinson's disease models.

SUMMARY OF THE INVENTION

The applicant has now found that the association comprising:
dry extract of: a) *Vicia faba*, b) *Uncaria rhyncophylla* and c) liquorice root and
coenzyme Q10,
can be effectively used as a coadjuvant to improve the quality of life (QOL) of a patient suffering from movement disorders and in particular for the treatment of Parkinson's disease.

In fact, as demonstrated in the experimental tests reported hereinafter, the applicant has found that this association, when compared with the activities of the single extracts, is able to show a preventive action as it is able to:
determine a significant reduction in nitrite levels, nitrosative stress indices;
reduce the activity of lactate dehydrogenase, in turn a sign of tissue damage;
and, at the same time, although to a slightly lesser extent than the single extracts a), b) and c), it is able to
reduce the levels of 8-iso-PGF2α (8-iso Prostaglandin F2α), an index of lipoperoxidation, an intermediate action among the botanical components;
reduce the levels of dopaminergic turnover, evaluated as a DOPAC/DA ratio,
where DOPAC is the main dopamine metabolite "DA" (FIG. 4).

Therefore this association, unlike the single dry extracts a), b) and c) and of the coenzyme Q10, besides exerting an effective therapeutic action in the acute phase of movement disorders and in particular Parkinson's, is also able to elicit a preventive action against these pathologies that is decidedly higher than the one of the single extracts.

DESCRIPTION OF THE FIGURES

The legend of the following
FIG. 1 shows the effect of the association (formulation) object of the invention on the levels of nitrites in the striatum in comparison with the analogous ones obtained using the single extracts a), b) and c) and those obtained on the negative control (striatum treated only with vehicle) and on the positive control (striatum on which only the vehicle and LPS had been administered).

FIG. 2 shows the effect of the association (formulation) indicated in the graph on the levels of LDH in the striatum compared with those obtained using the single extracts a), b)

and c) and those obtained with the negative control (treated with the vehicle alone) and with the positive control, namely the striatum treated with the vehicle and LPS.

Figure 3:
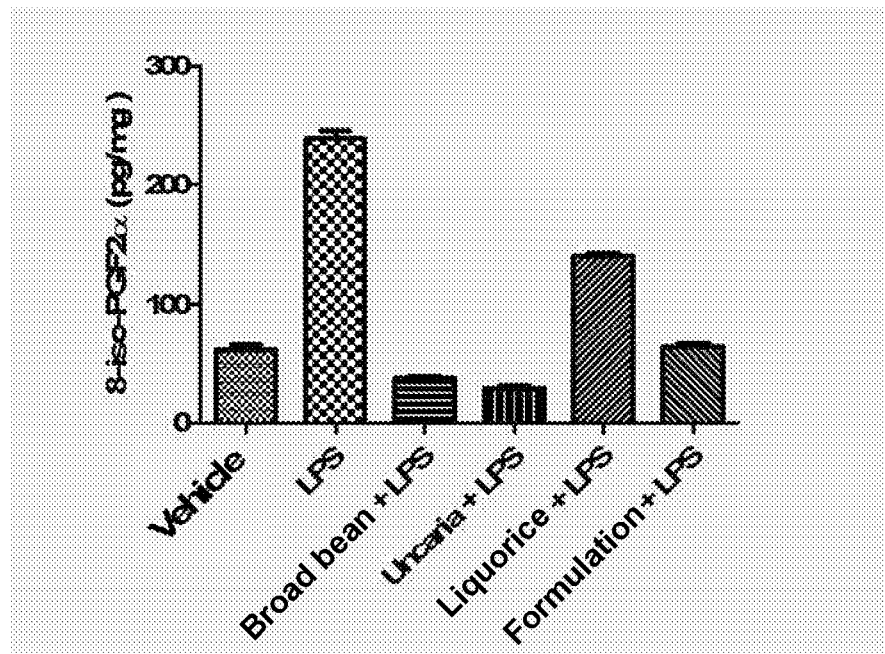

FIG. 3 shows the effect of the association (formulation) according to the present invention and indicated in the graph with the levels of 8-iso-PGF2α in the striatum compared with those obtained using the single extracts a), b) and c) and those obtained with the negative control treated with the vehicle alone and with the positive control, namely the striatum treated with the vehicle and LPS.

Figure 4:
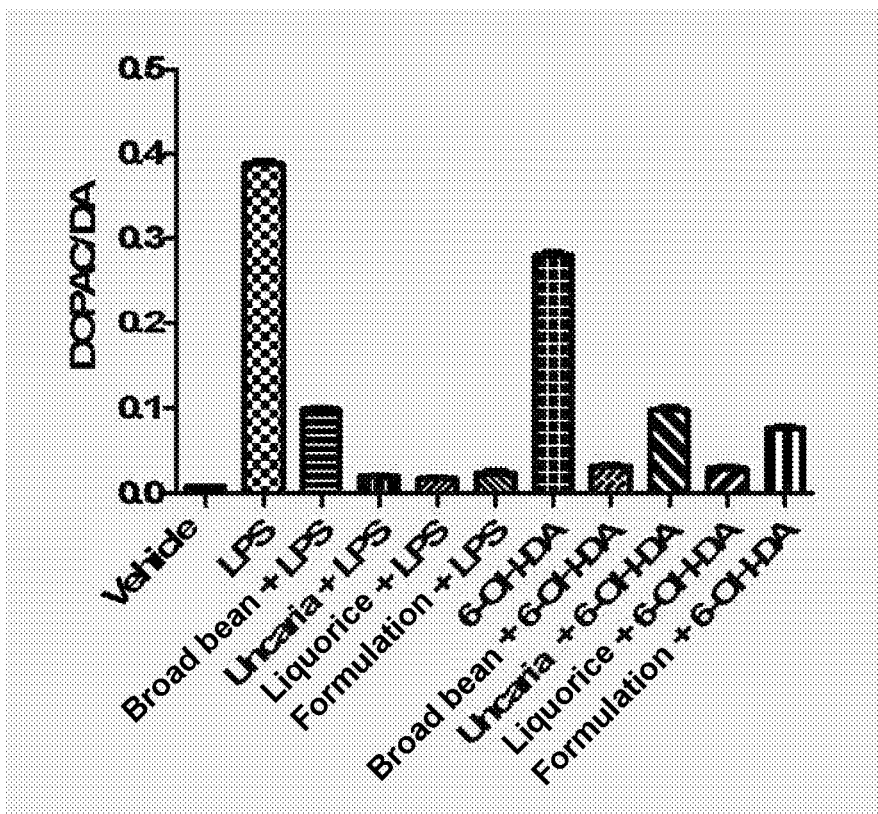

FIG. 4 shows the effect of the association according to the present invention and indicated in the graph with formulation on the levels of DOPAC/DA in the striatum compared to those obtained with the single extracts a), b) and c) and respectively with the negative controls of the striatum treated with the vehicle alone and with the positive controls treated with LPS and 6-OH-DA, respectively.

DETAILED DESCRIPTION OF THE INVENTION

As also stated in the part relating to the state of the art of the present description, for the purposes of the present invention, the definition "movement disorders" groups together a vast number of diseases characterized by reduced motor skills and/or by the presence of involuntary movements, namely movements that are hardly controllable with willpower. They are preferably primary parkinsonian syndromes (Parkinson's disease, multi-systemic atrophy, progressive supranuclear palsy, cortico-basal degeneration, dementia with lewy bodies), secondary parkinsonian syndromes (so-called vascular, infectious, post-infectious, post-traumatic parkinsonisms and parkinsonisms due to non-conventional agents, parkinsonisms due to environmental, iatrogenic, metabolic toxic factors) and forms of parkinsonism associated with hereditary diseases of the central nervous system (Wilson's disease, Westphal variant of Huntington's, Hallervorden Spatz disease). Preferably, the movement disorder treated with the association according to the present invention is Parkinson's disease. For the purposes of the present invention, the definition "comprising the following components" does not exclude the presence of further components other than those expressly listed and cited; whereas the definition "consisting of the following components" has a more restrictive meaning, as it excludes the presence of other components besides those expressly mentioned. The dry Vicia faba extract is preferably obtained from the fruits. Preferably, the association for use according to the present invention comprises at least one vitamin selected from vitamin C and E. More preferably, the association for use according to the present invention comprises both vitamins.

Even more preferably, the association for use according to the present invention is constituted by:
dry extract of: a) Vicia faba, b) Uncaria rhyncophylla and c) liquorice root and
coenzyme Q10,
vitamin C and vitamin E.

Preferably, the association for use according to the present invention is contained in an oral formulation, preferably a food supplement in combination with suitable excipients and/or diluents.

Preferably, the food supplement is in the form of a single-dose sachet containing:
between 800 and 1200 mg, preferably 1000 mg, of dry extract of a),
between 80 and 120 mg, preferably 100 mg, of dry extract of b),
between 30 and 70 mg, preferably 50 mg, of dry extract of c) with a percentage content by weight, calculated on the total weight of dry extract of c), of minimum 10%, more preferably between 18 and 22%, of glycyrrhetinic acid,
between 30 and 70 mg, preferably 50 mg, of coenzyme Q10,
between 60 and 100 mg of vitamin C, preferably 80 mg,
between 10 and 14 mg, preferably 12 mg, of vitamin E.

Preferably, the oral formulation or more particularly the food supplement comprising the association for the purpose of the invention is preferably administered only once a day.

An example of the daily single-dose sachet formulation is reported in the following Table 1 for illustrative but non-limiting purposes, in which the active ingredients and the relative quantities are reported but neither the excipients nor their quantities are reported, excipients that, however, are of the conventional type and well known to those skilled in the art.

TABLE 1

Formulation of the active ingredients per single-dose sachet with a total weight including the excipients of about 4 g to be dissolved in approximately 250 ml of water.

| COMPONENTS | DOSES FOR 1 sachet |
|---|---|
| BROAD BEAN - Vicia faba - Dry Extract a) | 1 gr* |
| Uncaria rhyncophylla - Dry extract b) | 100 mg |
| LIQUORICE root - Dry extract c) with a percentage content between 18%-22% by weight, based on the weight of the dry extract c), of glycyrrhetinic acid | 50 mg |
| Vitamin C - E300 ascorbic acid | Corresponding to 80 mg Vitamin C |
| Vitamin E acetate - liquid | Corresponding to 12 mg Vitamin E |
| Coenzyme Q10 (UBIDECARENONE) | 50 mg |

*this extract is obtained from 4 g of fresh plant (preferably fresh fruit)

The following experimental test reported below demonstrates the efficacy both in terms of prevention and efficacy on neurodegeneration processes of the association object of the present invention.

EXPERIMENTAL TEST

1. Experimental Model

The single samples, after solubilisation, are tested according to an ex vivo experimental model.

Stimulation with the extracts is carried out by adding scalar concentrations of the solution to the culture medium. The effects will be evaluated through the quantitative determination of specific markers of neurotransmission, oxidative stress and inflammation due to the morphological and structural alterations of a chronic inflammation of the brain tissue. To this end, specific sections of striatum nucleus, prefrontal cortex and hippocampus subjected to treatment with pro-inflammatory and degenerative stimuli such as LPS and 6-hydroxydamine have been removed from the rat brain.

The effect of supplementation on the culture medium was then evaluated by evaluating the following parameters:
levels of dopamine and of its main metabolite (DOPAC): ratio DOPAC/DA;

activity of lipoperoxidation biomarkers and key enzymes in oxidative stress and in tissue damage such as lactate dehydrogenase, catalase, myeloperoxidase, cyclooxygenase and nitric oxide synthase.

The used dosages of the single extracts in the tests are the same as those present in the complete formulation and respect the relationships between the various components of the commercial formula.

2. Results and Discussion

The present work investigated the role of the components of a food supplement based on broad bean, *Uncaria rhyncophylla*, liquorice, coenzyme Q10, in an experimental model of neuroinflammation and Parkinson's disease, ex vivo.

In this experimental model, biopsies of rat striatum were incubated at 37° C. in a controlled atmosphere for 4 h with a medium consisting of the phosphate buffer known as "Dulbecco's Buffer".

In particular, the tissue was incubated under the following experimental conditions:
Vehicle: stimulation with Dulbecco's Buffer only;
LPS: stimulation with the additional Dulbecco's Buffer of the bacterial lipopolysaccharide (LPS);
Food Supplement: stimulation with additional Dulbecco's Buffer of the bacterial lipopolysaccharide (LPS) and of the food supplement.
6-OH-DA: stimulation with the additional Dulbecco's Buffer of 6-OH-DA;
Food Supplement: stimulation with the additional Dulbecco's Buffer of 6-OH-DA.

The treatment of the isolated rat tissue with LPS is a validated experimental model of inflammation capable of reproducing inflammatory and oxidative damage in vivo (Phytother Res. 2016 September; 30 (9): 1513-8)

On the other hand, the treatment with 6-OH-DA reproduces ex vivo the neurodegeneration in Parkinson's disease (Neurotox Res. 2007 April; 11 (3-4): 151-67.).

In this experimental condition it is observed an increase in markers of oxidative stress and tissue damage, such as nitrites (nitrites) and lactate dehydrogenase (LDH), and a reduction in dopamine levels in the striatum.

On the other hand, the treatment of striatum biopsies subjected to pro-inflammatory stimuli with drugs and plant extracts with antioxidant/anti-inflammatory activity can prevent the onset of tissue damage and the pathological increase of markers of oxidative stress and tissue damage.

Figure 1:
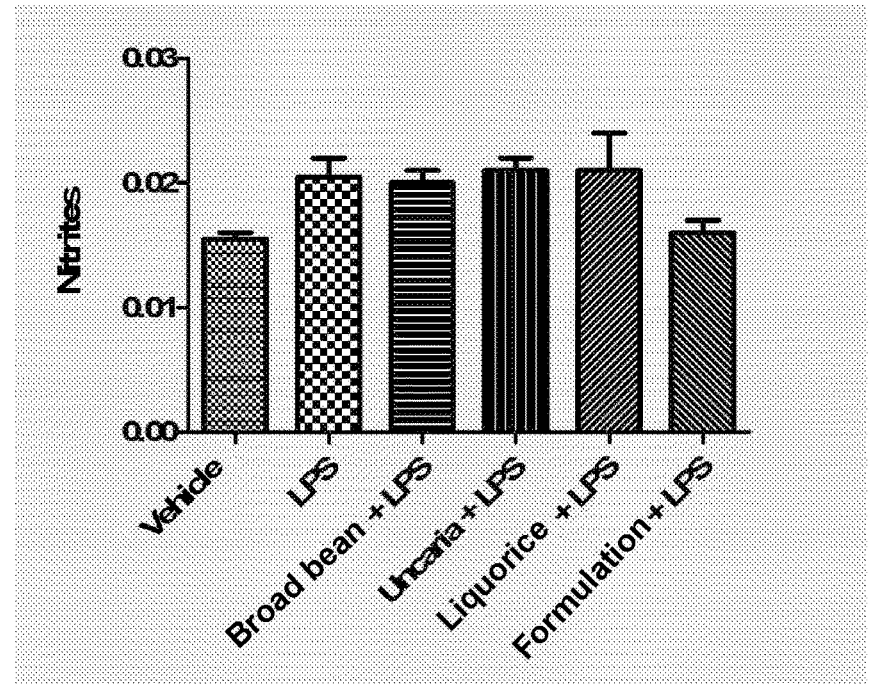
FIGS. 1-4 is shown below:
LPS=lipopolysaccharide
6-OH-DA=6-hydroxydopamine
Dulbecco's Buffer: untreated control
8-iso-PGF2α: 8-iso Prostaglandin F2α
DOPAC: 3,4-dihydroxyphenylacetic acid (dopamine metabolite)
DA: Dopamine
DOPAC/DA: a measure of DA turnover. The ratio is increased in the case of neurodegeneration
APOPTOSIS: programmed cell death
Figure 2:
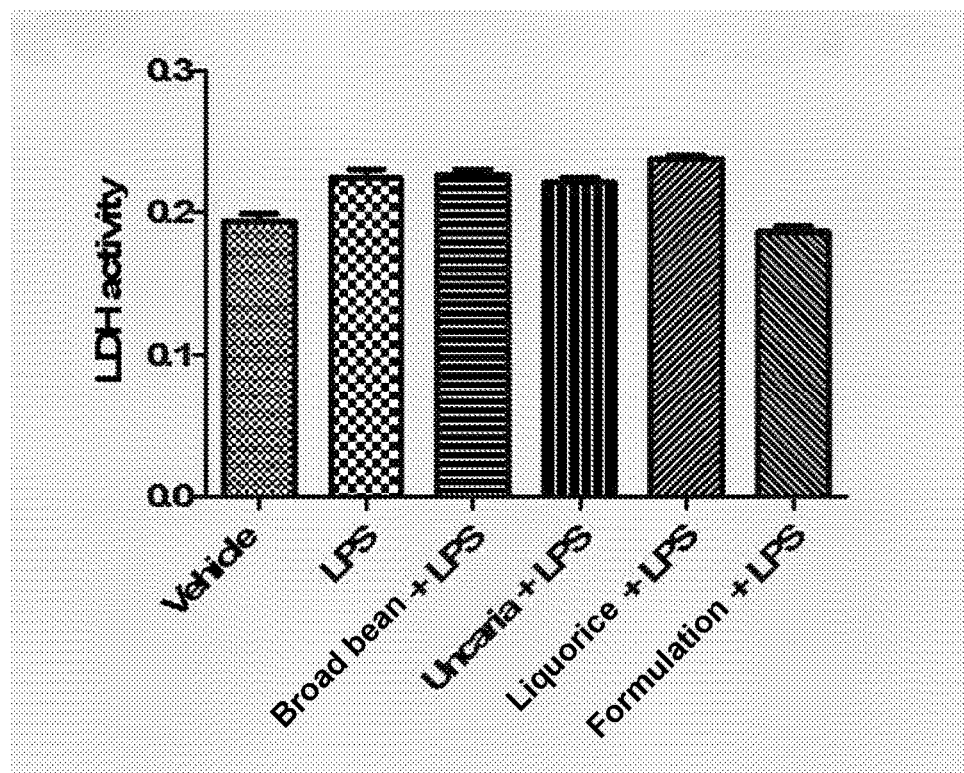

In this context, it has been observed that the use of the food supplement has proved to be capable of:
determining a significant reduction in the levels of nitrites, in the indexes of nitrosative stress, which is a stronger action than the one of the single components (FIG. 1);
reducing the activity of lactate dehydrogenase, which is in turn a sign of tissue damage, which is a stronger action than the one of the single components (FIG. 2);
reducing the levels of 8-iso-PGF2α (8-iso Prostaglandin F2α), an index of lipoperoxidation, an intermediate action between the botanical components (FIG. 3);
reducing the levels of dopaminergic turnover, evaluated as a DOPAC/DA ratio, where DOPAC is the main metabolite of dopamine "DA" (FIG. 4).

The single plant components (broad bean, *Uncaria* and liquorice) were found to be ineffective or less effective than the formulation in preventing oxidative damage.

As regards the activity of the single components and of the supplement on dopaminergic turnover (DOPAC/DA ratio), it is observed that in the tissues stimulated with LPS the formulation has a protective action higher than that of the broad bean and comparable to that of liquorice and *Uncaria* (FIG. 4), which show inhibitory effects on dopaminergic turnover and on the apoptotic pathway, respectively.

On the other hand, on the striatum tissue stimulated with the neurotoxin 6-OH-dopamine, it is observed that the food supplement has an action slightly lower than the single vegetable components, resulting more active than the *Uncaria* and slightly less active if compared to liquorice and broad bean. If compared with the positive control (6-OH-DA), however, the supplement impactfully decreases the DOPAC/DA ratio to justify the effectiveness of the mixture.

Therefore, it can be concluded that, at the level of the striatum stimulated with LPS, the food supplement has a stronger protective effect, if compared to the single components, which could derive from a multitarget antioxidant action. On the other hand, the effectiveness, although just slightly lower if compared to the single extracts, shown in a model of Parkinson's disease induced by 6-OH-dopamine, supports the use of the supplement as a protective agent capable of reducing the inflammatory and oxidative state in the brain that characterizes the acute phase of neurodegenerative diseases.

BIBLIOGRAPHY

1. Nicola Vanacore et al. Epidemiologia Dei Parkinsonismi. Centro Nazionale di Epidemiologia, Sorveglianza e Promozione della Salute, Istituto Superiore di Sanità. www.epicentro.iss.it
2. Alessandro Alimonti et al. Morbo di Parkinson: bio monitoraggio degli elementi chimici e del danno ossidativo. Rapporti ISTISAN 05/23. 2005
3. J. M. Ramirez-Moreno et al. Broad bean (*Vicia faba*) consumption and Parkinson's disease: a natural source of L-dopa to consider. Neurologia. 2015
4. Jinguo Hu et al. LC-MS determination of L-DOPA concentration in the leaf and flower tissues of six faba bean (*Vicia faba* L.) lines with common and rare flower colors. Functional Foods in Health and Disease 2015
5. J M Rabey et al. Improvement of Parkinsonian features correlate with high plasma levodopa values after broad bean (*Vicia faba*) consumption. Journal of Neurology, Neurosurgery, and Psychiatry. 1992
6. Mohseni Mehran S. M. et al. Simultaneous Determination of Levodopa and Carbidopa from Fava Bean, Green Peas and Green Beans by High Performance Liquid Gas Chromatography. Journal of Clinical and Diagnostic Research. 2013
7. Biswajit Pal et al. Evaluation of anti-Parkinson's activity of *Uncaria rhynchophylla* in 6-hydroxy dopamine lesioned rat model. International Journal of Applied Research. 2015
8. Borra Kartika et al. Herbal Treatment Of Parkinsonism: A Review. International Journal of Pharmaceutical Sciences Review and Research. 2010
9. Ka-Kit Chua et al. A Randomized Controlled Trial of Chinese Medicine on Nonmotor Symptoms in Parkinson's Disease. Hindawi Parkinson's Disease. 2017
10. Muhammad Usman Mirza et al. Glycyrrhetinic acid and E.resveratroloside act as potential plant derived compounds against dopamine receptor D3 for Parkinson's disease: a pharmacoinformatics study. Drug Design, Development and Therapy (Dovepress). 2014

11. E Mazzio et al. High throughput Screening to Identify Natural Human Monoamine Oxidase B Inhibitors. Phytother. Res. 2013

12. Huajun Jin et al. Mitochondria-Targeted Antioxidants For Treatment Of Parkinson's Disease: Preclinical And Clinical Outcomes. Biochim Biophys Acta. 2014

The invention claimed is:

1. Association, consisting of:
    dry extract of: a) *Vicia faba*, b) *Uncaria rhyncophylla* and c) liquorice root;
    coenzyme Q10;
    vitamin C and vitamin E,
    as coadjuvant in the treatment of movement disorders.

2. Association according to claim 1, contained in an oral formulation, in combination with suitable excipients and/or diluents.

3. Association according to claim 2, wherein said oral formulation is a food supplement.

4. Association according to claim 3, wherein said food supplement is in the form of a single-dose sachet containing:
    between 800 and 1200 mg of dry extract of a);
    between 80 and 120 mg of dry extract of b);
    between 30 and 70 mg of dry extract of c) containing a minimum 10% by weight of glycyrrhetinic acid calculated on the total weight of the dry extract c);
    between 30 and 70 mg of coenzyme Q10;
    between 60 and 100 mg of vitamin C;
    between 10 and 14 mg of vitamin E.

5. Association according to claim 2, wherein said oral formulation is administered only once a day.

6. Association according to claim 4, wherein said single-dose sachet contains
    1000 mg of dry extract of a);
    100 mg of dry extract of b);
    50 mg of dry extract of c) containing a minimum of 10% by weight, between 18 and 22% of glycyrrhetinic acid calculated on the total weight of the dry extract c);
    50 mg of coenzyme Q10;
    80 mg of vitamic C; and
    12 mg of vitamin E.

7. Association according to claim 1, wherein said movement disorder is Parkinson's disease.

* * * * *